US007125412B2

(12) United States Patent
Shifrin et al.

(10) Patent No.: US 7,125,412 B2
(45) Date of Patent: Oct. 24, 2006

(54) METHOD AND APPARATUS FOR INTRALUMINAL FIXATION OF INTRAVASCULAR DEVICES

(75) Inventors: Edward Shifrin, Raanana (IL); Mark Umansky, Haifa (IL); Mordehy Shvartsman, Haifa (IL); Gennady Nickelshpur, Haifa (IL); Wesley Moore, Los Angeles, CA (US)

(73) Assignee: Ruby Hill Ltd., Raanana (IL)

( * ) Notice: Subject to any disclaimer, the term of this patent is extended or adjusted under 35 U.S.C. 154(b) by 644 days.

(21) Appl. No.: 10/349,611

(22) Filed: Jan. 23, 2003

(65) Prior Publication Data

US 2003/0149441 A1    Aug. 7, 2003

(30) Foreign Application Priority Data

Feb. 3, 2002 (IL) ...................................... 147956

(51) Int. Cl.
*A61B 17/10* (2006.01)
(52) U.S. Cl. ..................................... 606/142
(58) Field of Classification Search ................ 606/151, 606/153, 139, 142, 143, 213, 215, 219, 174; 623/1.13, 1.23
See application file for complete search history.

(56) References Cited

U.S. PATENT DOCUMENTS 5,906,625 A * 5/1999 Bito et al. ................... 606/142
6,896,684 B1 * 5/2005 Monassevitch et al. ..... 606/142

\* cited by examiner

Primary Examiner—Kevin T. Truong
(74) Attorney, Agent, or Firm—William J. Sapone; Coleman Sudol Sapone P.C.

(57) ABSTRACT

The present invention rerlates to medical techniques, in particular, to methods and apparatus applied in minimally invasive vascular surgery to eliminate occlusion of blood vessel, using grafts and to prevent rupture of abdominal aorta using grafts or stent-grafts. More particularly, the present invention relates to methods and apparatus for locating and securing intravascular devices, substantially grafts, through a duct specially created by the surgeon to approach the blood vessel lumen. There is suggested a new and improved method for fixating an intravascular device to a blood vessel wall in combination with a new and improved stapler design based on this method. The stapler comprises a hollow body at the proximal end whereof there are mounted a guiding head and a die, and at the distal end, at a certain angle to the latter, a holding handle and a control lever, pivotally connected to this handle, and this control lever is operatively connected, via a movable pressure member, to a tip located inside the body, head and die. In the die there are disposed fastener means. The movement of control lever is converted into radial forces necessary for punching the wall of an intravascular device and surrounding blood vessel wall, location and fixation of fastener means, with simaltaneous bending of their ends. For maximum sinking of heads of fastening elements in the wall of an intravascular device, additional pushing members are movably mounted in radial slots of the die. The intravascular device, substantially graft, is fixated to a blood vessel wall, substantially aorta, via a set of at lest two staplers, and in each of the staplers there are disposed simultaneously several fastener means.

19 Claims, 13 Drawing Sheets

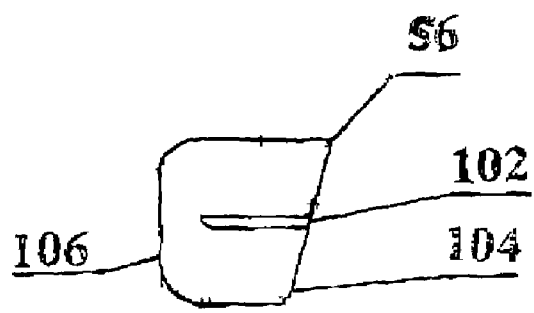
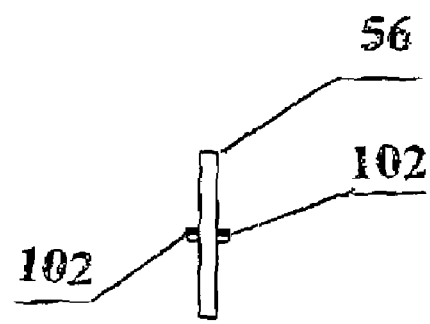
FIG. 8   FIG. 9
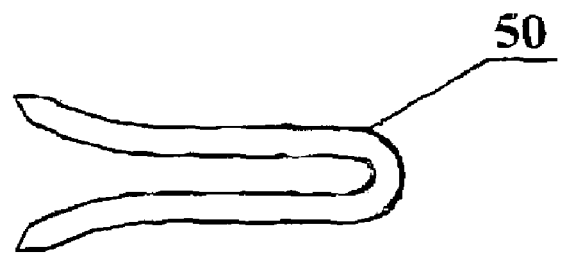
FIG. 10

C - C

IV

V

METHOD AND APPARATUS FOR INTRALUMINAL FIXATION OF INTRAVASCULAR DEVICES

BACKGROUND OF THE INVENTION

1. Field of the Invention

The present invention relates to medical techniques, in particular, to apparatus and methods used in minimally invasive vascular surgery using grafts for eliminating occlusion of blood vessels or stent-grafts for preventing rupture of abdominal aorta, as well as to methods for their location and fixation. More particularly, the present invention relates to methods and apparatus for securing intravascular devices, such as grafts or stent-grafts, to the walls of blood vessels in direction from inside these vessels to their outer surface.

2. Description of Related Art

Occlusion of great blood vessel resulting from formation of calcic or adipose deposits on their inner walls, or from thrombogenesis causes deterioration of blood supply to most important organs, such as the heart and brain, and to such dangerous situations for the patient, as infarction or insult.

To prevent occlusion of great blood vessels, in modern medicine there are widely used different methods of centura of main blood vessels based on minimally invasive surgery. In the course of centura, inside the main blood vessel, succesively, under X-ray control, there is introduced a guide, and over the latter a catheter with a balloon at the free end. When deposits of essential volume or a thrombus is detected inside the blood vessel, the balloon is inflated by pressure of fluid, so that the corresponding portion of the vessel expands and opens. In case it turns out to be insufficient, and the lumen in the blood vessel remains narrow, there is inserted inside the corresponding portion of this blood vessel a guide with a balloon, carrying on its outer surface a stent in compressed state. When liquid is delivered inside the balloon under pressure, the stent deploys, separates from the balloon and takes the desired position inside the blood vessel. All these manipulations are carried out under X-ray control. Fixation of the stent on the walls of a blood vessel is performed via elastic forces of material the stent is made of, the stent is usually shaped as a spring or has elastic members bearing up against the blood vessel wall or hooking thereon.

When the location of a stent for elimination of narrowing or occlusion of a blood vessel is insufficient, a surgical operation is performed for suturing in a natural or synthetic graft.

An aortic aneurysm (or its rupture) is a most common form of arterial aneurysms. It is a very common type of deteriorating disease affecting the ability of a lumen to conduct fluids and may be life threatening. The aortic aneurysm is a ballooning of the wall of an artery resulting from the weakening of the artery's wall due to disease or other conditions. Left untreated, the aneurysm will frequently rupture, resulting in loss of blood trough the rupture—the condition, which often leads to death.

The aorta is the main artery, which supplies blood to the circulatory system. The aorta arises from the left ventricle of the heart, passes upwards and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal region between the renal arteries and the iliac arteries. This portion of the abdominal aorta is particularly susceptible to weakening, resulting in an aortic aneurysm. Such an aneurysm is often located near the iliac arteries. An aortic aneurysm larger than about five centimetres in diameter in this section of the aorta is ominous. Left untreated, the aneurysm may rupture, resulting in rapid, and usually fatal, hemorrhaging. Typically, a surgical procedure is not performed on aneurysms smaller than five centimetres because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Beside synthetic grafts, there are developed and widely used all over the world particularly to prevent the rupture of the aorta wall intravascular devices of "stent-graft" type. They are inserted and positioned similar to stents. Fixation of a stent-graft on aorta walls is performed via elastic forces of the material of the stent-graft itself which usually has springy elements bearing up against the blood vessel wall or hooking thereon. When the forces of elastic or springy elements of the stent-graft are insufficient for its fixation in a blood vessel, the stent-graft may be displaced from the assigned position and moved along the aorta under the action of blood flow and peristelsic oscillations of walls of this blood vessel, and that is very dangerous for the patient.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, the common repair means is to deploy a stent-graft within the lumen of the affected aorta in the region of the aneurysm. These methods and devices have been developed to attempt to treat an aortic aneurysm without the attendant risks of intra-abdominal surgical intervention. Among them are inventions disclosed and claimed in Parodi, Juan C. et al., WO 010487A1 for Graft Device for Treating Abdominal Aortic Aneurysms and its patent family, including U.S. Pat. Nos. 5,219,355, 5,522,880, 5,571,171, 5,643,208, 5,683,452, 5,693,087, 6,102,942, EP 461791A1, EP 809980A3, EP 903118A2, EP 903119A3, EP 903120A3 etc.

Parodi discloses a stent-graft device for locating inside an aorta affected by an aneurysm causing the aorta to have an inner diameter smaller than the sum of inner diameters of the iliac arteries. The graft has an upper main tubular portion dividing into two pending graft limbs capable of accommodating together within the restricted inner diameter of the aorta without the restriction of the aorta affecting the diameter of the limbs. The limbs have respective distal end portion having diameters larger than the diameters of the graft limbs so as to be accommodated and retained within the iliac arteries Parodi's stent-graft is inserted using a tubular device also disclosed in his patent.

In other Parodi's patents there are disclosed stent-graft designs having a metal wire frame collapsible to a minimal size sufficient to insert the stent-graft into the artery through a puncture in its wall and expandable inside the aorta to a required size under the action of a radial force, such as a balloon. This frame is covered by a sheath which can contract and expand together with the frame under the action of external forces. Aforesaid stent-grafts are provided with means for mechanical fixation to the walls of the aorta or iliac arteries. Among those means we find balloon cuffs of a special shape at the stent-graft ends, see WO 010487A1, U.S. Pat. No. 5,522,880, U.S. Pat. No. 5,219,355, various hooks, elements shaped as scales, spirals and similar elements designed for fixation on the wall of the aorta or artery, see U.S. Pat. No. 5,911,733 Endovascular Expander of a Non-migrant Positioning, EP 948945A2 Endovascular Prosthesis with Fixation Means.

The problem of fixation of stents and stent-grafts inside the aorta and iliac arteries is PARTIALLY solved by other inventors likewise.

Lindenberg, Josef in EP 711135A1 discloses a stent with an improved anchorage in a vessel. The stent can be expanded from a radially contracted insertion state into a radially expanded positioning state such that in the radially expanded state at least one end has a larger radial extension than the remaining main body of the stent.

Samuels in U.S. Pat. No. 5,423,851 discloses a method and apparatus for affixing an endoluminal device to the walls of tubular structures within the body which utilizes incremental inflation of a balloon cuff to deploy radially projecting barbs attached to the cuff within plurality of recesses.

Kugler, Chad disclose in their patent WO 19943A1 a stent-graft comprising radially expandable portions attached to one another and anchored to the aorta walls by a radial force. This stent-graft can bend to match the aorta longitudinal section by relative angular displacement of its portions.

Houser, Russel in WO 15144A1 discloses a system and components for treating aortic aneurysms includes a reinforcing graft and combinations of fittings and rings for securing the graft to a host vessel, to branch vessels, for example the iliac, and renal arteries.

Edwin, Tarun et al., disclose in EP 868154A1 a structurally supported graft having a support structure with strain relief sections containing an internal surface, an external surface, or a wall thickness of a tubular graft member. The structural support forms a spiral about the tubular graft.

Numerous suggestions of stent-graft inventors present various hooks and anchor members, integral or not integral with the stent-graft frame to fixate the latter inside the aorta or iliac arteries. Such suggestions are disclosed in U.S. Pat. No. 6,015,431, EP 747020A2, EP 701800A1, EP 657147A2, EP 466518A2, U.S. Pat. No. 5,669,936, U.S. Pat. No. 6,004,347, U.S. Pat. No. 5,733,325, U.S. Pat. No. 5,104,399, U.S. Pat. No. 6,030,413.

All the above-mentioned inventions have, in our opinion, a common drawback, which consists in the fact that the stent-grafts fixation on the inner walls of the aorta and iliac arteries is not reliable enough and bring to many complications. Therefore, under the action of blood flow and peristaltic oscillations of artery walls, stent-grafts are displaced from their proper positions, which may have grave consequences for the patient and result in his death because of the aorta rupture.

3. The Prior Art

Closest to the present invention are inventions disclosed and claimed in Taheri, Syde, U.S. Pat. No. 5,843,169 for Apparatus and Method for Stapling Graft Material to a Blood Vessel Wall while Preserving the Patency of Orifices and inventions disclosed and claimed by Tanner, Howard, in U.S. Pat. No. 5,944,750 for Method and Apparatus for the Surgical Repair of Aneurysms, U.S. Pat. No. 5,957,940 for Fasteners for Use in the Surgical Repair of Aneurysms and U.S. Pat. No. 5,997,556 for Surgical Fastener.

Taheri, Syde in U.S. Pat. No. 5,843,169 discloses an apparatus for stapling graft material to a blood vessel wall comprising a stapling device, a balloon catheter, a sheath, and an inflation means.

The apparatus design suggested by Tahery is, in our opinion, inoperative as the radial force generated by a balloon is inadequate to insert a securing member shaped as a nail into the wall of the aorta or artery. It is especially unlikely if the wall of the aorta or artery is covered with calcium plaques.

Tanner, Howard in U.S. Pat. No. 5,944,750 discloses an attachment assembly and repair graft for securing to repair a vessel having an aneurysm therein. The attachment assembly comprises an attachment cuff such that the graft is not dimensionally dependent upon the size of the vessel. The apparatus also comprises a visualization apparatus for real time direct viewing of an interior of a vessel. A penetration apparatus is disclosed for use in forming treatment specific holes in a potentially calcified vessel wall, which facilitates thereafter the securing of the graft and attachment assembly to the vessel wall. An introducer sheath device is also disclosed that comprises a sealing assembly for preventing the loss of blood from the vessel during the insertion and subsequent removal of surgical components during the surgical procedure.

In U.S. Pat. No. 5,957,940 and U.S. Pat. No. 5,997,556, H. Tanner also discloses fasteners for use during a surgical procedure for securing surgical components to the blood vessel wall under a compressive force. According to the inventions, the fastener assemblies are shaped as a coiled spring or spiral or plurality of entwined coil springs or ring type fasteners including a plurality of rings.

All the described inventions by Howard Tanner have, in our opinion, a complicated and not adequately reliable design and limited functional possibilities. So, in particular, the apparatus for setting the securing elements cannot be brought in operative position inside iliac arteries having a small lateral diameter. Because of limited space it is impossible to bend the end of the apparatus working head for setting the securing elements in the stent-graft wall. The efficiency of this apparatus for drilling holes in the walls of the stent-graft, aorta and iliac arteries is doubted, especially if these walls are calcified and covered by calcium plaques. In general, we think that the apparatus presented by Howard Tanner can be used only inside the aorta and not inside iliac arteries. As far as the suggested securing elements are concerned, we believe that their fixation in the inner walls of the aorta and iliac arteries is not reliable enough. Therefore, under the action of blood flow and peristaltic oscillations of artery walls, the stent-graft may be displaced from its proper position, which may have grave consequences for the patient and may result in his death due to the aorta rapture.

And finally, there are known devices developed in France by Thierry Richard, Eric Perouse et al., such as "Surgical staple inserter", see U.S. Pat. No. 5,346,115; WO 9217117; EP 0533897 and "Surgical staple for tissue", see Pat. FR 2746292.

U.S. Pat. No. 5,346,115; WO 9217117; EP 0533897 describes a surgical staple inserter for joining two ducts such as a blood vessel and blood prosthesis. The staple inserter ejects staples in a radial direction relative to the axis of the ducts. In one embodiment, it includes a staple holder surrounded by the prosthesis and containing a series of staples arranged in at least one ring. All the staples are ejected simultaneously. The staple inserter also includes an anvil outside the organic duct, and a device for spacing apart the anvil and the staple holder in relation to their relative working position. Projections hold he prosthesis in place during the insertion of the staple holder into the ducts.

This device is essentially complicated in design, and the main drawback of it is that it is impossible to bend the ends of staples when they are extended from the device body outside, through the prosthesis and wall of the blood vessel. Therefore it is necessary to provide the device with anvils located outside the operated blood vessel, which makes the device itself and the whole surgical procedure for setting a stent-graft considerably more complicated and expensive.

Pat. FR 2746292 describes a surgical staple, which has a circular spiral formed of metallic wire. It extends on a complete spiral, which is augmented over part of its length. The staple can have a barbed end. The device for these staples inserting comprise a guide tube, extending towards the front by an inwardly curved section with a guide channel. At least a section of metal wire moves in the guide tube. A pusher moves the wire section towards the distal end of the guide tube.

This device also has some essential drawbacks. So it is a difficult procedure to set the staples, as it is necessary to achieve very precise positioning of the device relative to the prosthesis wall. It is impossible to set simultaneously several staples with this device design. Besides, an essential part of staples project inside the prosthesis, which may result in accelerated thrombogenesis in this inner lumen of the prosthesis.

In general, at present, the authors of the present invention have no information on any methods and apparatus for fixation of grafts and stent-grafts on the walls of a blood vessel from inside this vessel, which are developed, ready for full-scale production and applied in real life in minimally invasive surgery.

An object of the present invention is to provide reliable and relatively simple means for securing a graft, stent-graft or other intravascular devices to the wall of the aorta, iliac arteries or other arteries, in particular, a new and improved method for stapling and stapling apparatus based on this method.

Another object of the present invention is to provide suturing of the prosthesis to a blood vessel simultaneously over the entire perimeter of the connection, and assuring necessary strength and leak-proofness of this connection, including even such hard-to-reach spots as the aorta neck or the area directly under the renal arteries.

SUMMARY OF THE INVENTION

The present invention includes a method for intraluminal fixation of intravacular devices, such as grafts, stent-grafts, located inside blood vessels using minimally invasive surgery techniques.

This method does not cause grave injuries to the patient as it is as well performed using minimally invasive surgery techniques, from inside the blood vessel, substantially aorta, and using a special stapler.

The method includes several successive steps. At the first step there is created, by surgical procedure, a duct to approach the lumen of the blood vessel being operated, substantially the aorta, directly through the wall of this blood vessel. Then, through the duct thus opened, a special stapler with a corresponding intravascular device mounted thereon, substantially graft, is inserted into the lumen of the operated blood vessel, and this intravascular device is located in required position. Thereupon the stapler is brought into operative position necessary for securing the first end of intravascular device, in this case a graft to the wall of a blood vessel, substantially the aorta. Then follows checking of the matching of mutual location of the first end of intravascular device, place of its supposed securing to the wall of blood vessel, as well as the stapler working head with fastener means disposed in the die at its free end.

Next, in the stapler working head, there is created an axial force sufficient to act on fastener means. Due to this force, fastener means, extending from the die in radial direction, punch the wall of the intravascular device and surrounding blood vessel wall so, that the distal ends of these fastener means come in part outside the blood vessel and bend on its outer surface to form a rigid connection of the first end of intravascular device to the blood vessel wall. Then the stapler working head is withdrawn from the first end of the wall of intravascular device, whereby fastener means remain fixated in the wall of intravascular device and in the blood vessel wall, securing the first end of intravascular device to the corresponding portion of the blood vessel and preventing thereby any its displacement relative to this blood vessel. Further, the stapler is brought into inoperative position necessary for its free removal and removed from intravascular device and from the blood vessel.

At the next step there is made an incision in the intravascular device (stapler) to approach its lumen. Then another special stapler for securing the second end of this intravascular device to the wall of this blood vessel (aorta) is inserted through the duct prepared before and through the incision into the lumen of an intravascular device (graft). This stapler is brought into operative position, its working head with fastener means disposed in the die at its free end, is brought to the wall of intravascular device, at the spot of fastening its second end to the blood vessel wall. Then there is performed checking of the matching of mutual location of the second end of intravascular device, the place of its supposed securing to the blood vessel wall, as well as the working head of stapler with fastener means. When in the working head of this stapler there is created an axial force sufficient to act on fastener means, these fastener means, extending from the die in radial direction, punch the wall of intravascular device and surrounding wall of the blood vessel so, that distal ends of these fastener means come in part outside the blood vessel and bend on its outer surface, forming a rigid connection of the second end of intravascular device to the blood vessel wall. Then the working head of the other stapler is withdrawn from the wall of intravascular device, whereby fastener means remain fixated in the wall of intravascular device and in the blood vessel wall, securing the second end of intravascular device to the corresponding portion of the blood vessel and preventing thereby any its displacement relative to this blood vessel. Thereupon the stapler is brought into inoperative position necessary for its free removal from intravascular device and removed therefrom and from the blood vessel.

At the last step there are closed, by surgical procedure, the incision in intravascular device and the duct to approach the lumen of intravascular device and lumen of the operated blood vessel.

Due to the above described manipulations, there is formed a secure multiple-spot connection of intravascular device to the blood vessel wall preventing displacement of this intravascular device from a given position under the action of blood flow and peristelsic oscillations of the blood vessel wall.

According to the claimed method, the intravascular device, such as graft, may be secured to the blood vessel wall via at least one claimed stapler and using at least two fastener means simultaneously at least at two points. This is performed substantially close to one of the free ends of this intravascular device.

According to the present method, the ends of an intravascular device, such as a stent-graft, having a broad proximal part and bifurcated distal part, may be secured to the wall of a blood vessel (aorta) via a set of at least two staplers and using in each of them simultaneously at least two fastener means. The set contains at least one first stapler for securing the broad proximal part of the stent-graft to the aorta wall and at least one second stapler for securing the bifurcated distal part of stent-graft to the aorta wall. In this case the proximal end of stent-graft having a broad proximal part, is secured to the wall of blood vessel (aorta) in the aorta neck area, via the first of staplers contained in the set of staplers, and using simultaneously at least two said fastener means.

The distal end of stent-graft having a bifurcated distal part, is secured to the aorta wall via a second of staplers contained in the set, and using simultaneously at least two fastener means. It is performed close to the free end of one or the second of the branches of bifurcated distal part of this stent-graft.

The distal end of stent-graft having a bifurcated distal part is secured to the aorta wall via the second of staplers contained in the set, and using simultaneously at least two fastener means. It is performed close to the free end of one or the second of branches of the bifurcated distal part of this stent-graft.

And at last, according to the claimed method, the stent-graft may be secured to the aorta wall using as well at least two fastener means close to the free end of both branches of the bifurcated distal part of stent-graft.

The claimed invention also includes a stapler for intraluminal fixation of intravascular devices, substantially grafts, located inside blood vessels, using minimally invasive surgery techniques.

This stapler comprises a hollow body, substantially cylindrical in shape, having a proximal end and a distal end with a holding handle extending therefrom at a certain angle, not exceeding 90 degrees, and a control lever pivotally mounted on this holding handle. At the proximal end of the hollow body there are rigidly secured, coaxially with this body and successively in direction towards the free end of stapler—a die and guiding head forming in combination the working head of this stapler.

Inside the hollow body there is disposed a pressure rod, having a longitudinal axis, proximal end and distal end. This pressure rod is a means for transmitting axial force from the control lever to fastener means and for converting this axial force into radial forces applied to each of these fastener means. The pressure rod is operatively connected by its distal end to the control lever, spring-loaded, has a thrust collar close to its proximal end, and at its proximal end there is rigidly secured a tip, mounted to reciprocate inside the die and guiding head.

The die for locating fastener means is shaped as a barrel having a proximal end, distal end, substantially cylindrical generatrix and inner axial cavity open on the side of the barrel distal end and terminating in a bottom at the barrel proximal end. This bottom has through, evenly arranged radial slots, and on its end face presented to the guiding head-recesses with grooves for location of fastener means. These recesses with grooves are coaxial with radial slots and provided with means for setting apart the ends of fastener means disposed along the axes of grooves, right up to the cylindrical generatrix and having substantially a V-section. Each recess with a groove is closed with an individual lid shaped as an annular segment and rigidly connected to the end face of said die. These recesses with grooves have substantially the same depth relative to the end face of said die bottom.

In another embodiment of the die the recesses with grooves may have substantially different depth relative to the end face of this die bottom. In this embodiment each of the recesses is covered with an individual lid shaped as an annular segment, and having an inner surface matching the corresponding recess. The recesses with grooves may have at least two different depths relative to the end face of the die bottom. In this case the recesses with grooves of different depth are arranged alternately.

The stapler may also have a guiding head substantially with a cylindrical generatrix, flat or rounded free end, radial slots disposed in the head body and coming onto its generatrix, as well as with an outer bulge at the opposite end of this head. The head is located by its bulge right up to individual lids on the end face of the die, and the radial slots of the guiding head are coaxial with the radial slots of the die and in these slots there is movably disposed the proximal end of the pressure rod. The outer diameter of the cylindrical generatrix of guiding head is smaller than the outer diameter of said bulge and die by a double value of distance assuring fastener means removal from the die, when this fastener means is entirely extended in radial direction.

The guiding head may be hollow, and its rounded free end detachable, capable of being periodically mechanically connected to this head.

The guiding head may be also hollow, with a generatrix shaped as a truncated cone facing by its greater base the rounded free end of this head. At last, the guiding head may be hollow, with a curved generatrix, substantially shaped as a paraboloid, widening towards the free end of this head. In both last embodiments of the guiding head its free end is detachable, capable of periodical mechanical connection to this head. Besides, the outer diameter of generatrix of the guiding head close to the bulge is less than the outer diameter of the bulge and the outer diameter of the die by a double value of distance assuring the removal of fastener means from the die, when this fastener means is entirely extended in radial direction.

The fastener means are substantially U-shaped and arranged radially in grooves of the die, and are radially extendable from these grooves under the action of radial forces. The free ends of fastener means are disposed on both sides of means for setting apart the ends of these fastener means located along the axes of grooves, right up to the cylindrical generatrix of the die.

The means for setting apart the ends of fastener means have substantially a V-shaped section and lateral guiding faces, substantially curved, concave and diverging from one another in direction from the die center to its cylindrical generatrix. This allows bend outward the free ends of fastener means when they are extended from the die under the action of radial forces. Means for setting apart the ends of fastener means may have lateral guiding faces, substantially radial, concave and diverging from one another in direction from the die center to its cylindrical generatrix.

At the free end of pressure rod there is rigidly mounted a tip with pressure ribs evenly arranged in radial directions about the longitudinal axis of this tip at its proximal end and integral with one another. All the pressure ribs have an outer inclined pressure surface and oriented in radial direction so, that each rib, in the course of reciprocal movement of the pressure rod passes in part through the corresponding radial slot of the die and corresponding radial slot of the guiding head to cooperate with a corresponding fastener means.

Each pressure rib of the tip is shaped substantially as a right triangle with the greater leg oriented along the longitudinal axis of the pressure rod and hypotenuse forming an outer inclined pressure surface. The vertices of all triangular pressure ribs converge to one point at the free end of the pressure rod facing the rounded end of the guiding head.

In another embodiment of the tip each its pressure rib is shaped substantially as a right-angled trapezium with one side oriented along the longitudinal axis of this pressure rod, and a second side forming an outer inclined pressure surface The smaller bases of all trapezoidal pressure ribs converge to the end face at the free end of this tip presented to the rounded end of this guiding head.

The outer inclined pressure surfaces of ribs of this tip are disposed at an angle of 3 to 40 degrees relative to the longitudinal axis of this tip.

In another embodiment of the claimed stapler the means for transmitting axial force from the pressure rod to fastener means and for converting this axial force into radial forces applied to each of these fastener means may be not only the tip with pressure ribs, but also additional pushing members. These additional pushing members are shapes as thin plates movably mounted in radial slots of the die in radial directions about the longitudinal axis of the tip and provided with bearing projections located in recesses of the die. In this case the inner ends of additional pushing members are capable to cooperate with outer inclined pressure surfaces of the tip ribs, and the outer ends of these additional pushing members are capable to cooperate with fastener means disposed in corresponding die grooves.

And, at last, there is an embodiment of the stapler, wherein the die, guiding head, fastener means located in the die grooves, as well as additional pushing members movably mounted in radial slots of the die, form, in combination, a single set, detachable from the body of this stapler and capable of subsequent replacement by other, similar interchangeable sets.

Besides, the stapler may be additionally provided with an optical system for observing the positioning of the working head of this stapler relative to the surface of a corresponding intravascular device, as well as the location on this surface of fastener means for securing the intravascular device to the wall of a blood vessel. The optical system includes at least an optical lens connected via optical fibers with an optical monitor located at the surgeon's working place. In his case at least one of the optical fibers serves for lighting up the spots of location of fastener means for securing the intravascular device to the blood vessel wall.

BRIEF DESCRIPTION OF THE DRAWINGS

The invention will now be described in conjunction with the following drawings in which like reference numerals designate like elements and wherein:

FIG. 8-9 are side and front views of the additional pushing member;

FIG. 10 is a general view of a fastener means;

FIG. 15-17 are individual lids for grooves of the die according to the first embodiment, their shape, longitudinal section and close-up;

DETAILED DESCRIPTION OF PREFERRED EMBODIMENTS

The preferred embodiments of the present invention are described below. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

The most preferred embodiments of a stapler, according to the present invention, are shown in drawing FIGS. 1 and 2–28.

The present invention (FIG. 1) includes a stapler 1 for intraluminal fixation of intravascular devices, substantially grafts 3, located inside blood vessels, using minimally invasive surgery techniques.

Figure 1:
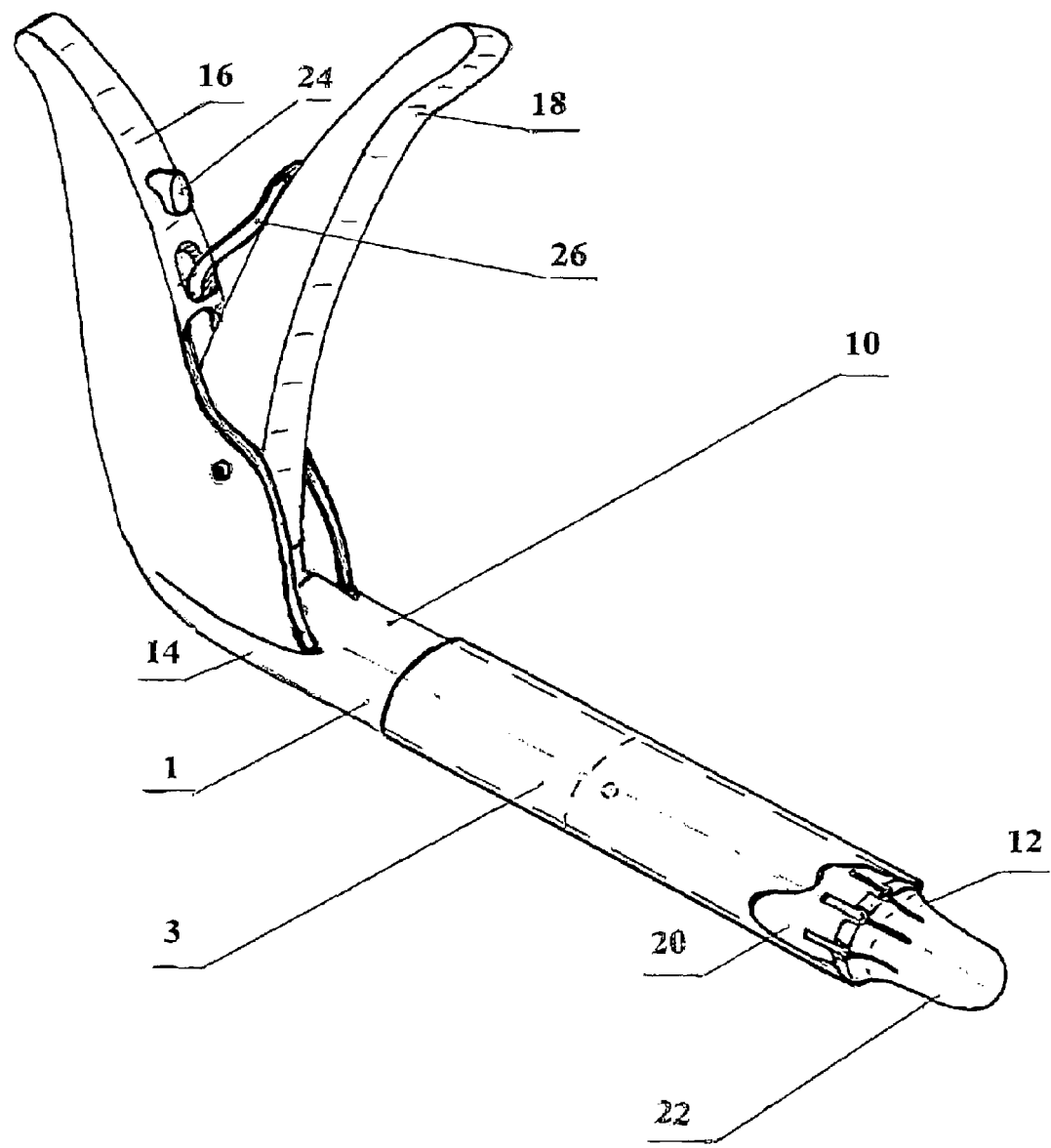
FIG. 1 is a perspective view of a stapler apparatus according the first embodiment of the present invention.
Figure 2:
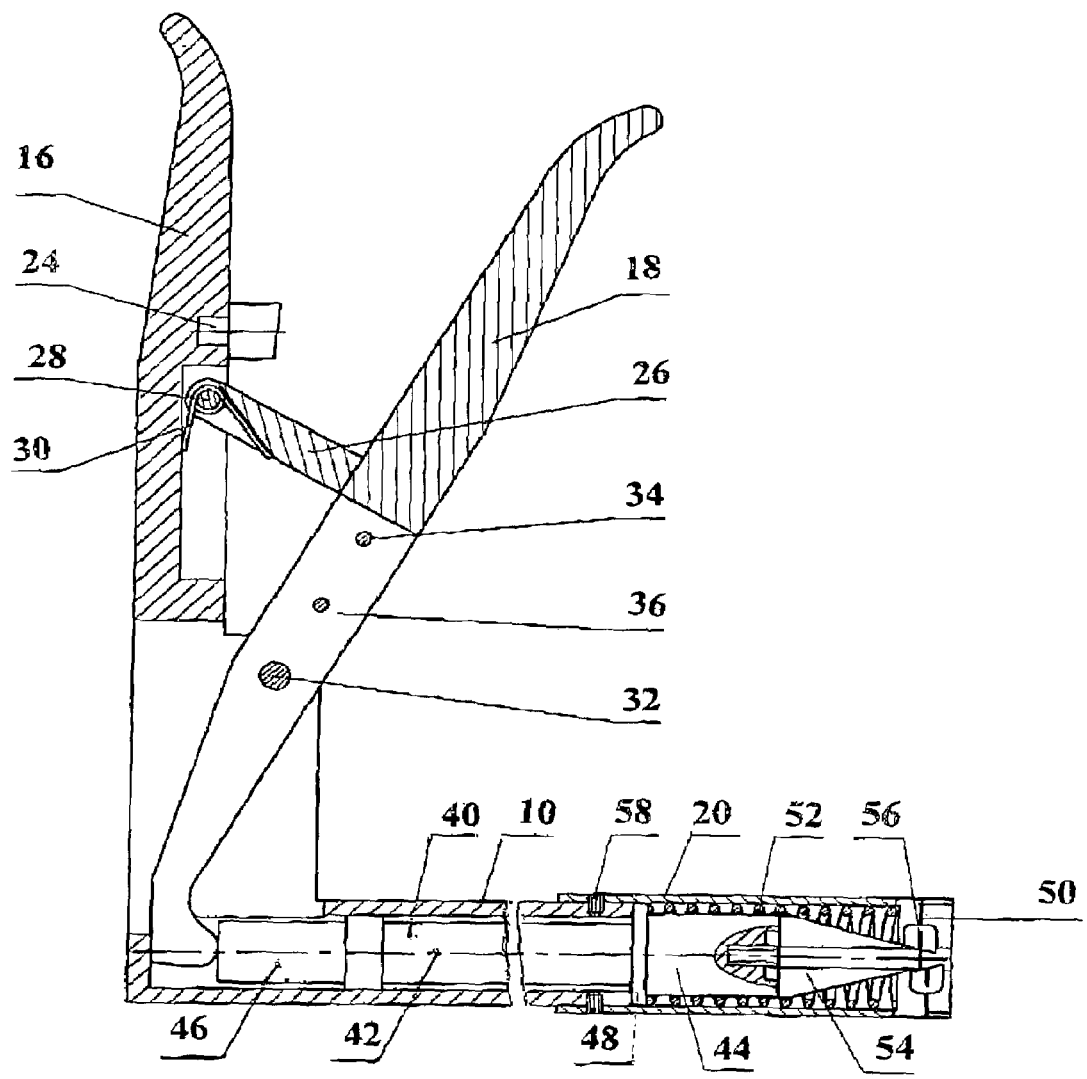
FIG. 2 is a longitudinal section of the stapler, according to the second embodiment of the present invention, with the pressure rod in initial position.
Figure 3:
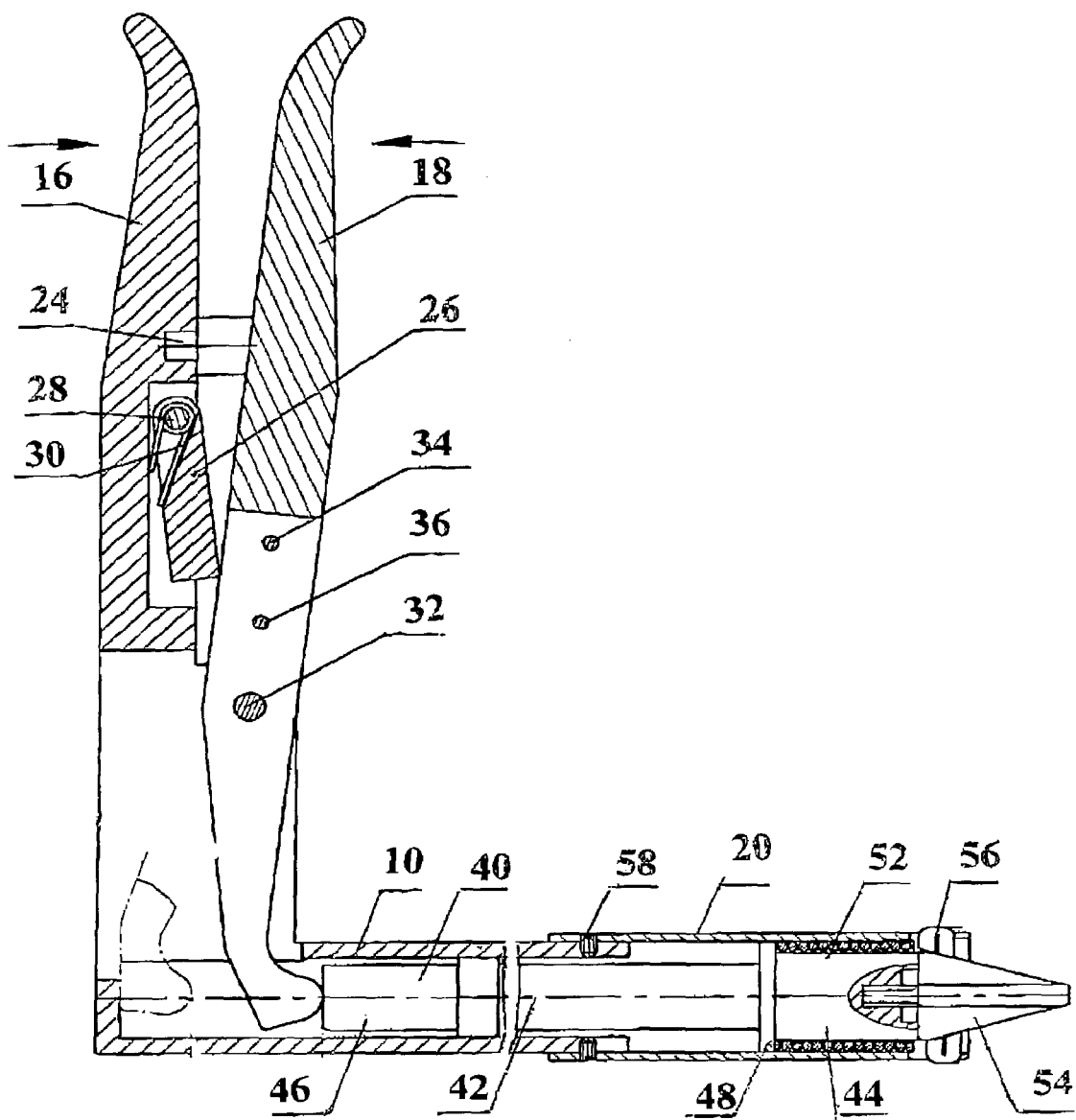
FIG. 3 is a longitudinal section of the stapler, according to the second embodiment of the present invention, with the pressure rod in final position.
Figure 4:
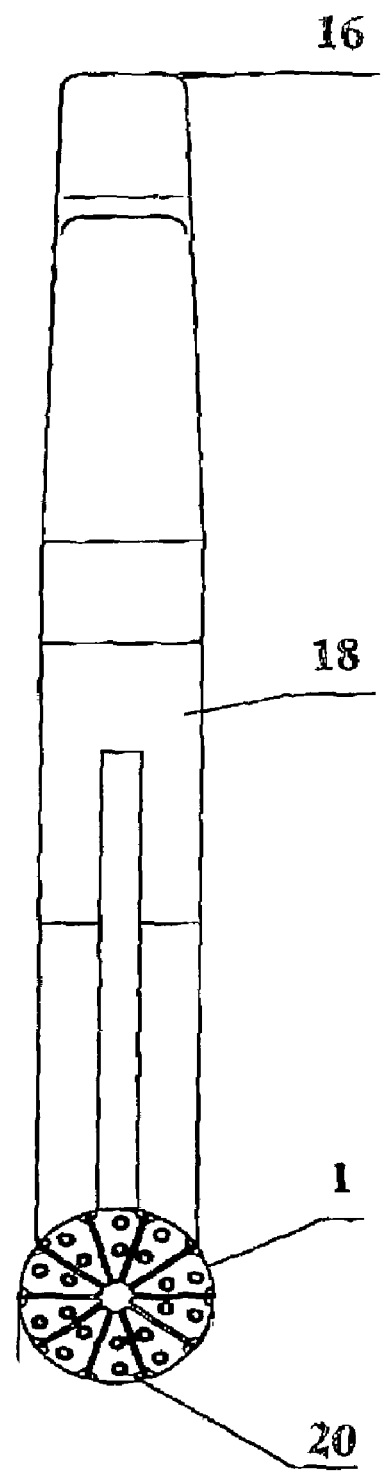
FIG. 4 is a front view of the claimed stapler, according to the second embodiment of the present invention.
Figure 5:
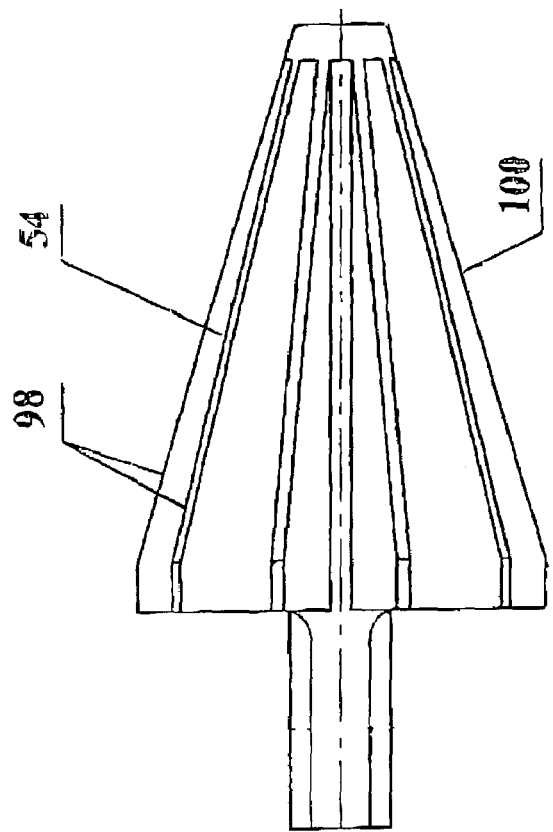
FIG. 5-7 are views of the tip and pressure rod.
Figure 6:
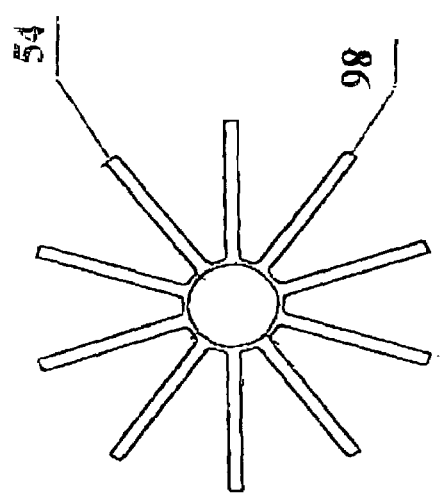
Figure 7:
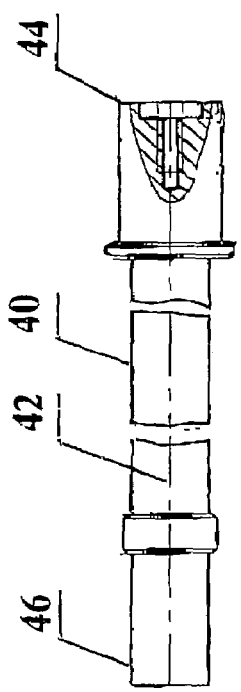
Figure 11:
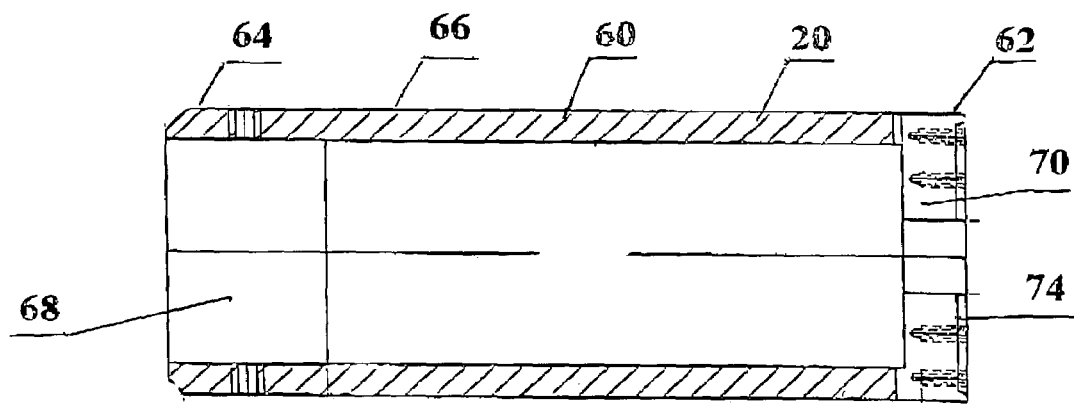
FIG. 11-17 is the first embodiment of the stapler die—its longitudinal section, front view, local section and close-up of a groove.

Stapler 1 comprises a hollow body 10, substantially cylindrical in shape (FIG. 1), having a proximal end 12 and a distal end 14 with a holding handle 16 extending therefrom at a certain angle, not exceeding 90 degrees, and a control lever 18 pivotally mounted on this holding handle. At the proximal end 12 of the hollow body 10 there are rigidly secured, coaxially with this body and successively in direction towards the free end of stapler—a die 20 and guiding head 22 forming in combination the working head of this stapler 1. On holding handle 16 there are mounted a stop 24 and lock 26 to prevent accidental pressing on control lever 18 (FIG. 1).

In the drawings (FIG. 2, 3) there is shown the longitudinal section of stapler 1 according to its second embodiment, and in the drawing (FIG. 4) its front view.

Lock 26 (FIG. 2) of stapler 1 is pivotally mounted on a pin 28 and loaded with a spring 30. Control lever 18 is pivotally mounted on pin 32 and may consist of two parts rigidly connected together via fastening elements 34 and 36—screws or rivets.

Inside the hollow body 10 (FIGS. 2, 3 and 7) there is disposed a pressure rod 40, having a longitudinal axis 42, proximal end 44 and distal end 46. This pressure rod 40 is a means for transmitting axial force from the control lever 18 to fastener means 50 (FIG. 10) and for converting this axial force into radial forces applied to each of these fastener means 50. The pressure rod 40 (FIG. 2, 3) is operatively connected by its distal end 46 to the control lever 18, loaded with a spring 52, has a thrust collar 48 close to its proximal end 44. At the proximal end 44 of pressure rod 40 there is rigidly secured a tip 54 (FIG. 5, 6), mounted to reciprocate inside the die 20 and guiding head 22. In the embodiment shown in drawings (FIG. 2, 3) the stapler is provided with additional pushing members 56 (FIG. 8, 9). The die 20 is mounted on the hollow body 10 by screws 58.

Figure 12:
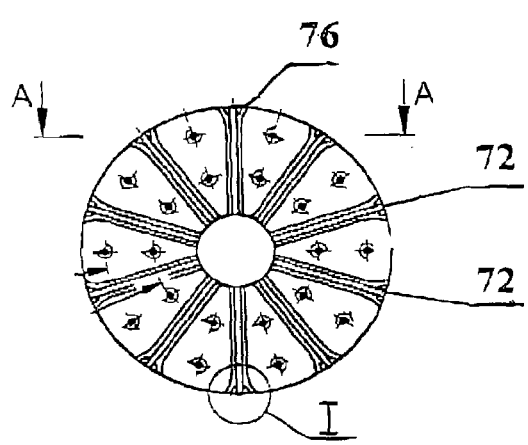
Figure 13:
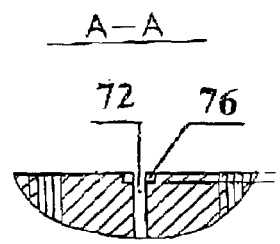
Figure 14:
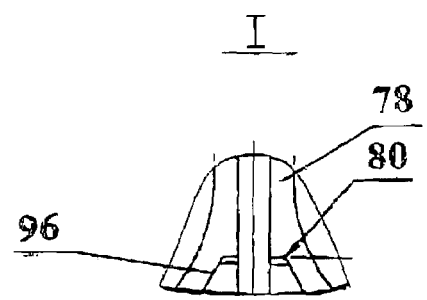
Figure 15:
Figure 16:
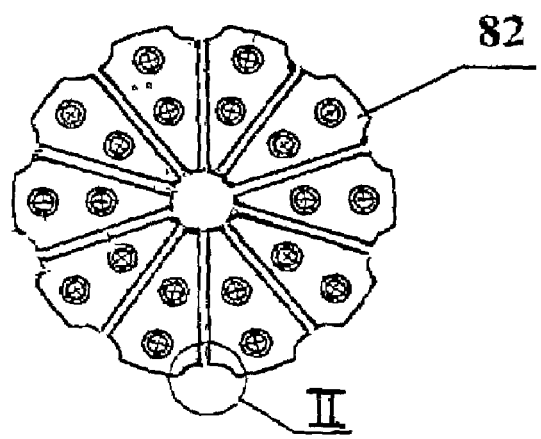
Figure 17:
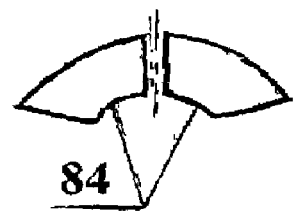
Figure 18:
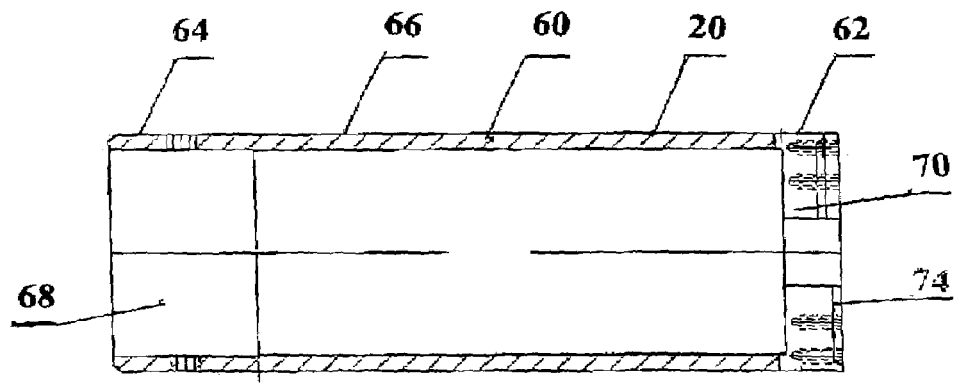
FIG. 18-21 is the second embodiment of the die of the claimed stapler—its longitudinal section, front view, local section and close-up of a groove.

The die 20 for locating fastener means 50 (FIGS. 11–17 and 18–26) is shaped as a barrel 60 (FIG. 11, 18) having a proximal end 62, distal end 64, substantially cylindrical generatrix 66 and inner axial cavity 68 open on the side of the barrel 60 distal end 64 and terminating in a bottom 70 at the barrel 60 proximal end 62. This bottom 70 has through, evenly arranged radial slots 72 (FIG. 12, 19), and on its end face 74 presented to the guiding head 22—recesses 76 with grooves 78 for location of fastener means 50 (FIG. 12-14). These recesses 76 with grooves 78 are coaxial with radial slots 72 and provided with means 80 for setting apart the ends of fastener means 50 disposed along the axes of grooves 78, right up to the cylindrical generatrix 66 of die 20 and having substantially a V-section. Each recess 76 with a groove 78 is closed with an individual lid 82 (FIG. 15-17) shaped as an annular segment and rigidly connected to the end face 74 of die 20. In outer corners of lids 82, close to the location of means 80, recesses 84 are made (FIG. 17). In the embodiment shown in drawings (FIG. 11-17) recesses 76 with grooves 78 have substantially the same depth relative to the end ace 74 of the bottom 70 of die 20. Thus there is provided even arrangement of fastener means 50 in one cross section of graft 3.

Figure 19:
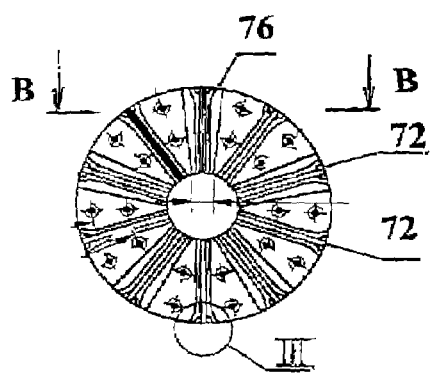
Figure 20:
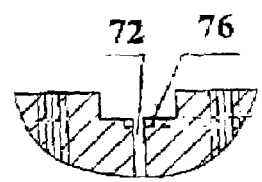
Figure 21:
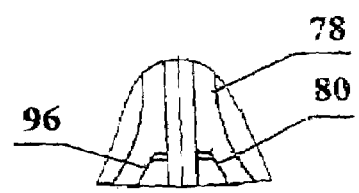
Figure 23:
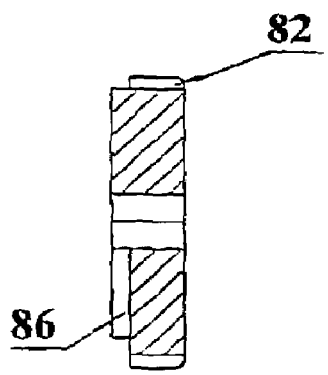
FIG. 22-26 are individual lids for grooves of a die according to the second embodiment, their shape, longitudinal section and close-ups.
Figure 22:
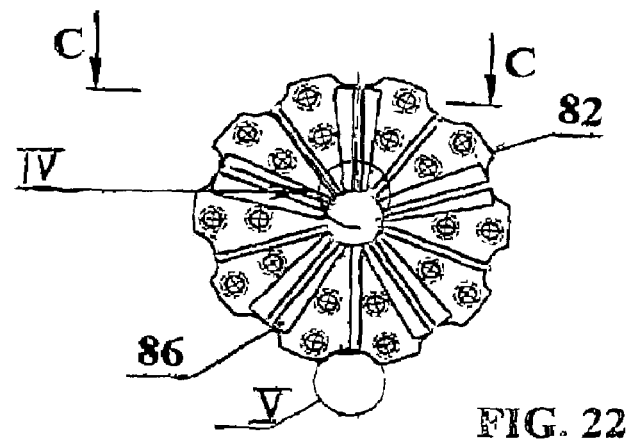
Figure 24:
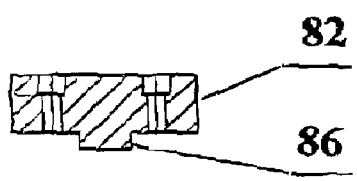
Figure 25:
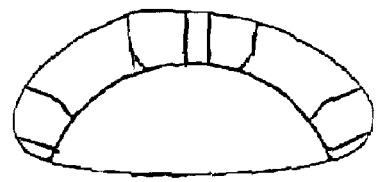
Figure 26:
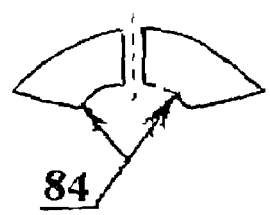

In another embodiment of the die 20 shown in the drawings (FIG. 18-26) when the recesses 76 with grooves 78 have substantially different depth relative to the end ace 74 of bottom 70 of this die 20. In this embodiment each of the recesses 76 is covered with an individual lid 82 (FIG. 22-26) shaped as an annular segment, and having an inner surface matching the corresponding recess 76, i. e. provided with a projection 86. Recesses 76 with grooves 78 in this embodiment of the die 20 (FIG. 22-26) may have at least two different depths relative to the end face 74 of bottom 70 of die 20. In this case the recesses 76 with grooves 78 of different depth are arranged alternately (FIG. 19). Thereby there is provided uneven arrangement of fastener means 50 mounted in two parallel cross sections of graft 3, which, in the authors' opinion, assures more secure connection of graft 3 to a blood vessel.

Stapler 1 may also have a guiding head 22 (FIG. 27) substantially with a cylindrical generatrix 88, flat or rounded free end 90, radial slots 92 evenly disposed in the body of head 22 and coming onto its generatrix 88, as well as with an outer bulge 94 at the opposite end of head 22. In this case head 22 is located by its bulge 94 right up to individual lids 82 on the end face 74 of the die 20, and the radial slots 92 of the guiding head 22 are coaxial with the radial slots 72 of the die 20 and in these slots there is movably disposed the proximal end 54 of the pressure rod 40. The outer diameter of the cylindrical generatrix 88 (FIG. 27) of guiding head 22 is smaller than the outer diameter of bulge 94 and die 20 by a double value of distance assuring fastener means 50 removal from the die 20, when this fastener means is entirely extended in radial direction.

Figure 27:
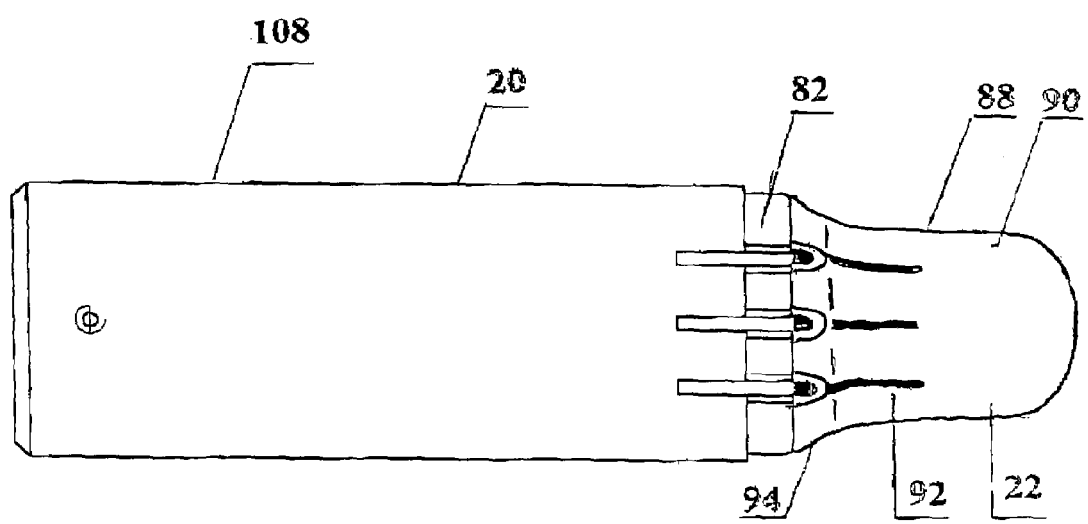
FIG. 27-28 are views of one of detachable heads used in the claimed stapler.
Figure 28:
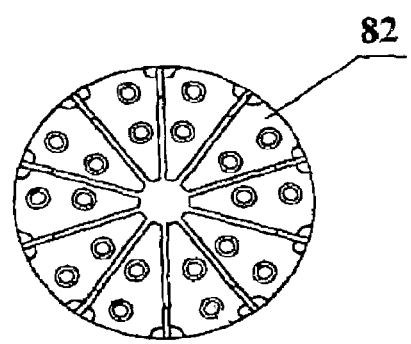

The guiding head 22 may be hollow, and its rounded free end 90 detachable, capable of being periodically mechanically connected to this head 22 (FIG. 27).

The guiding head 22 may be also hollow, with the generatrix 88 shaped as a truncated cone facing by its greater base the rounded free end 90 of this head 22 (not shown in the drawings). At last, the guiding head 22 may be hollow, with a curved generatrix, substantially shaped as a paraboloid, widening towards the free end 90 of this head (not shown in the drawings). In both last embodiments of the guiding head 22 its free end 90 is detachable, capable of periodical mechanical connection to this head 22. Besides, the outer diameter of generatrix 88 of the guiding head 22 close to the bulge 94 is less than the outer diameter of the bulge 94 and the outer diameter of the die 20 by a double value of distance assuring the removal of fastener means 50 from the die, when this fastener means is entirely extended in radial direction.

The fastener means 50 (FIG. 10) are substantially U-shaped and arranged radially in grooves 78 of the die 20, and are radially extendable from these grooves 78 under the action of radial forces. The free ends of fastener means 50 are disposed on both sides of means 80 for setting apart the ends of these fastener means 50 located along the axes of grooves 78, right up to the cylindrical generatrix 66 of the die 20.

The means 80 for setting apart the ends of fastener means 50 (FIG. 14) have substantially a V-shaped section and lateral guiding faces 96, substantially curved, concave and diverging from one another in direction from the die 20 center to its cylindrical generatrix 66. This allows bend outward the free ends of fastener means 50 when they are extended from the die 20 under the action of radial forces. Means 80 for setting apart the ends of fastener means 50 (FIG. 21) may have lateral guiding faces 96, substantially radial, concave and diverging from one another in direction from the die 20 center to its cylindrical generatrix 66.

At the free end of pressure rod 40 there is rigidly mounted a tip 54 (FIG. 5-7) with pressure ribs 98 evenly arranged in radial directions about the longitudinal axis of this tip 54 at its proximal end and integral with one another. All the pressure ribs 98 have an outer inclined pressure surface 100 and are oriented in radial direction so, that each rib 98, in the course of reciprocal movement of the pressure rod 40, passes in part through the corresponding radial slot 72 of the die 20 and corresponding radial slot 92 of the guiding head 22 to cooperate with a corresponding fastener means 50.

Each pressure rib 98 of the tip 54 is shaped substantially as a right triangle with the greater leg (FIG. 5-6) oriented along the longitudinal axis of the pressure rod 54 and hypotenuse forming an outer inclined pressure surface 100. The vertices of all triangular pressure ribs 98 converge to one point at the free end of the tip 54 facing the rounded end of the guiding head.

In another embodiment of the tip 54 each its pressure rib 98 is shaped substantially as a right-angled trapezium with one side oriented along the longitudinal axis of this pressure rod, and a second side forming an outer inclined pressure surface 100. The smaller bases of all trapezoidal pressure ribs 98 converge to the end face at the free end of this tip 54 presented to the rounded end 90 of this guiding head 22.

The outer inclined pressure surfaces 100 of ribs 98 of this tip are disposed at an angle of 3 to 40 degrees relative to the longitudinal axis of this tip.

In another embodiment of the claimed stapler 1 the means for transmitting axial force from the pressure rod 40 to fastener means 50 and for converting this axial force into radial forces applied to each of these fastener means 50 may be not only the tip with pressure ribs, but also additional pushing members 56 (FIG. 8, 9). These additional pushing members 56 are shaped as thin plates movably mounted in radial slots 72 of the die 20 in radial directions about the longitudinal axis of the tip 54 and provided with bearing projections 102 located in recesses 76 of the die 20 In His case the inner ends 104 of additional pushing members 56 are capable to cooperate with outer inclined pressure surfaces 100 of the tip 54 ribs 98, and the outer ends 106 of these additional pushing members 56 are capable to cooperate with fastener means 50 disposed in corresponding die 20 grooves 78.

And, at last, there is an embodiment of stapler 1, wherein the die 20, guiding head 22, fastener means 50, located in the die 20 grooves 78, as well as additional pushing members 56 movably mounted in radial slots 72 of the die 20, forms in combination, a single set 108 (FIG. 27) detachable from the body 10 of this stapler 1 and capable of subsequent replacement by other, similar interchangeable sets 108.

Besides, the stapler 1 may be additionally provided with an optical system for observing the positioning of the working head of this stapler 1 relative to the surface of a corresponding intravascular device—graft 3, as well as the location on his surface of fastener means 50 for securing the intravascular device—graft 3 to the wall of a blood vessel (not shown in the drawings). The optical system includes at least an optical lens connected via optical fibers with an optical monitor located at the surgeon's working place. In this case at least one of the optical fibers serves for lighting up the spots of location of fastener means 50 for securing the intravascular device—graft 3 to the blood vessel wall.

Figure 29:
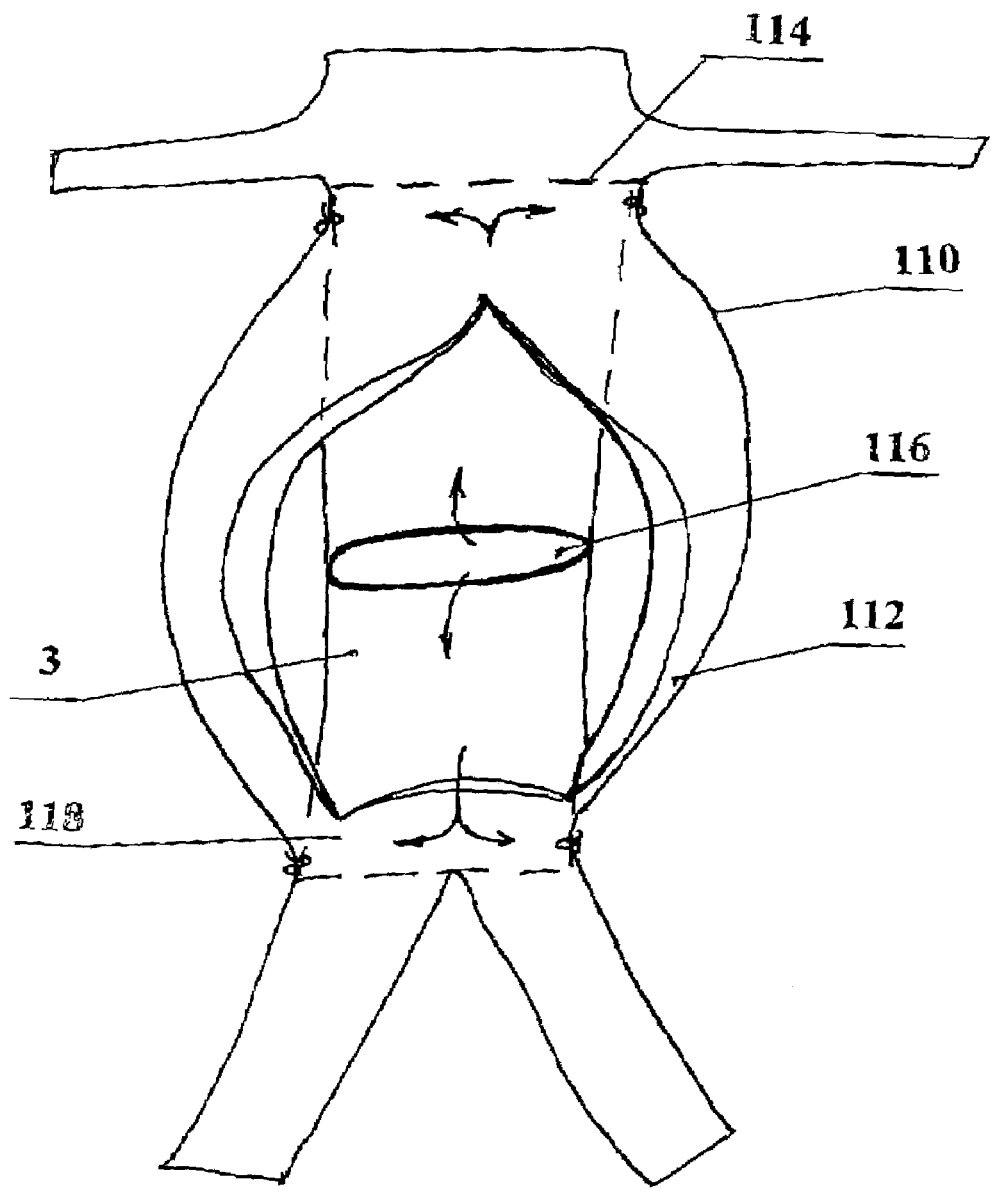
FIG. 29-30 are diagrams of locating a graft and stent-graft using a set of claimed staplers.
Figure 30:
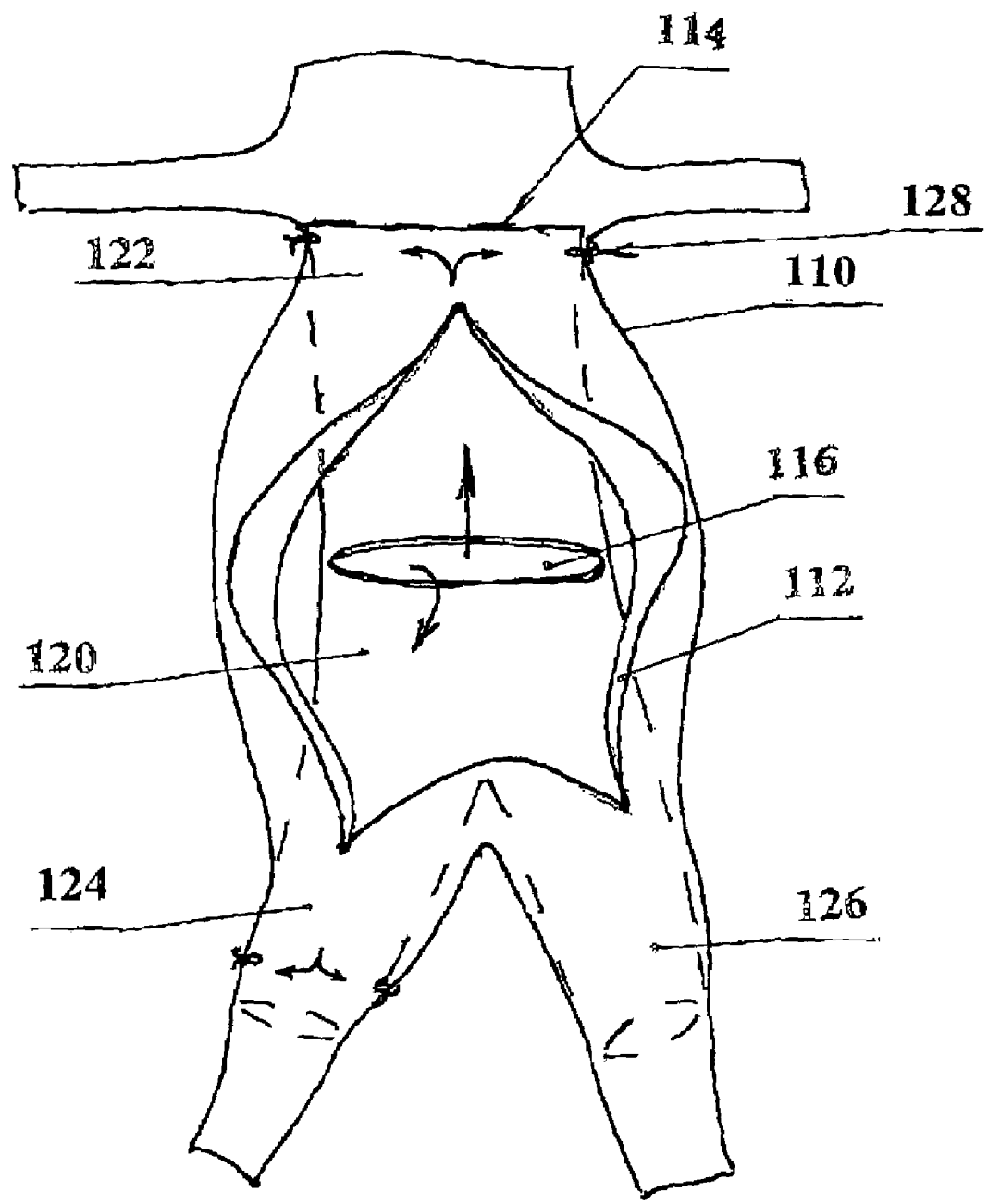

The present invention (FIG. 1) includes, besides stapler 1, a method for intraluminal fixation of an intravacular device, such as grafts 3 to the wall of a blood vessel, substantially aorta 110 (FIG 29).

Let us consider the fixation of graft 3 as an example of the claimed method for fixating an intravascular device. The method includes several successive steps (FIG. 29). At the first step there is created, by surgical procedure, a duct 112 to approach the lumen of the blood vessel being operated, substantially the aorta 110, directly through the wall of this blood vessel (aorta). Then, through the duct 112 thus opened, a special stapler 1 (FIG. 1) with a corresponding intravascular device mounted thereon, substantially graft 3, is inserted into the lumen of the operated blood vessel, substantially aorta 110, and this graft 3 is located in required position. Thereupon the stapler 1 is brought into operative position necessary for securing the first end of intravascular device, in this case a graft 3, to the wall of a blood vessel, substantially the aorta 110. Then follows checking of the matching of mutual location of the first end 114 of graft 3, place of its supposed securing to the wall of aorta 110, as well as the stapler 1 working head with fastener means 50 disposed in the die 20 at its free end.

Next, in the stapler 1 working head, there is created an axial force sufficient to act on fastener means 50. Due to this force, fastener means 50, extending from the die 20 in radial direction, punch the wall of the intravascular device-graft 3 and surrounding aorta 110 wall so, that the distal ends of these fastener means 50 come in part outside the aorta 110 wall and bend on its outer surface to form a rigid connection of the first end 114 of graft 3 to the aorta 110 wall. Then the stapler 1 working head is withdrawn from the first end of the wall of aorta 110, whereby fastener means 50 remain fixated in the wall of graft 3 and in the aorta 110 wall, securing the first end of graft 3 to the corresponding portion of aorta 110 and preventing thereby any its displacement relative to this aorta 110. Further, the stapler 1 is brought into inoperative position necessary for its free removal and removed from graft 3 and from aorta 110.

At the next step there is made an incision 116 in the graft 3 to approach its lumen. Then second special stapler 1 for securing the second end 118 of this graft 3 to the wall of aorta 110 is inserted through the duct prepared before and through the incision into the lumen of graft 3. This stapler 1 is brought into operative position, its working head with fastener means 50 disposed in the die 20 at its free end, is brought to the wall of graft 3, at the spot of fastening its second end to the aorta 110 wall. Then there is performed checking of the matching of mutual location of the second end 118 of graft 3, the place of its supposed securing to the aorta 110 wall, as well as the working head of stapler 1 with fastener means 50. When in the working head of this second stapler 1 there is created an axial force sufficient to act on fastener means 50, these fastener means 50, extending from the die 20 in radial direction, punch the wall of graft 3 and surrounding wall of the aorta 110 so, that distal ends of these fastener means 50 come in part outside the aorta 110 and bend on its outer surface, forming a rigid connection of the second end 118 of graft 3 to the aorta 110 wall. Then the working head of the other stapler 1 is withdrawn from the wall of graft 3, whereby fastener means 50 remain fixated in the wall of graft 3 and in the aorta 110 wall, securing the second end 118 of graft 3 to the corresponding portion of aorta 110 and preventing thereby any its displacement relative to this aorta 110. Thereupon the stapler 1 is brought into inoperative position necessary for its free removal from graft 3 and removed therefrom and from the aorta 110.

At the last step there are closed, by surgical procedure, the incision 116 in the graft 3 and the duct 112 to approach the lumen of graft 3 and lumen of the operated aorta 110.

Due to the above described manipulations, there is formed a secure multiple-spot connection of graft 3 to the aorta 110 wall preventing displacement of this graft 3 from a given position under the action of blood flow and peristelsic oscillations of the aorta 110 walls.

According to the claimed method, the ends of an intravascular device, such as a stent-graft 120 (FIG. 29), having a broad proximal part 122 and bifurcated distal part 124 and 126 may be secured to the aorta 110 wall via a set of at least two staplers 1 and using in each of them simultaneously at least two fastener means 50. The set contains at least one first stapler for securing the broad proximal part 122 of stent-graft 120 to the wall of aorta 110 and at least one second stapler for securing the bifurcated distal part 124 and 126 of stent-graft 120 to the wall of aorta 110. In his case the end of stent-graft having a broad proximal part 122, is secured to the wall of aorta 110 in the aorta 110 neck 128 area, via the first of staplers 1 contained in the set of staplers, and using simultaneously at least two said fastener means 50.

The distal end of stent-graft 120 having a bifurcated distal part 124 and 126, is secured to the aorta 110 wall via a second of staplers 1 contained in the set, and using simultaneously at least two fastener means 50. It is performed close to the free end of one 124 or the second 126 of the branches of bifurcated distal part of this stent-graft 120.

And at last, according to the claimed method, the stent-graft 120 may be secured to the aorta 110 wall using as well at least two fastener means 50 close to the free end of both branches 124 and 126 of the bifurcated distal part of stent-graft 120.

Application of the new and improved method for fixation in combination with a new stapling device—stapler 1 based on this method allows, in the opinion of authors, to solve the problem of providing secure and relatively simple means for fixatying intravascular devices to blood vessel walls. In particular, their application will permit to solve the problem of fixating stent-graft 120 to the aorta 110 wall or fixating grafts and other similar devices to blood vessel walls when these devices posess no sufficient fixation of themselves to prevent their duplacement from given positions.

While this invention has been described in conjunction with specific embodiment thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defied in the following claims.

The invention claimed is:

1. A stapler for intraluminal fixation of intravascular devices, substantially grafts, located inside blood vessels using minimally invasive surgery techniques, the stapler comprising:
   i) a hollow body, substantially of cylindrical shape, having a proximal end and distal end, the distal end have a holding handle extending therefrom at a certain angle and control lever, pivotally mounted thereon, and at the proximal end there are rigidly secured, coaxial with said hollow body and in succession to one another in direction to the free end of said stapler, a die and guiding head forming in combination the working head of said stapler;
   ii) a pressure rod disposed inside said hollow body, having a longitudinal axis, proximal end and distal end, said pressure rod is operatively connected by its distal end to said control lever, and its proximal end is capable of reciprocating inside said die and said head;
   iii) said die for locating fastener means shaped as a barrel, having a proximal end, distal end, substantially cylindrical generatrix and inner axial cavity, open on the side of said barrel distal end and terminating in a bottom at said barrel proximal end, the bottom has through, evenly arranged radial slots, and on its end face presented to the guiding head—recesses with grooves for locating fastener means, these recesses with grooves are coaxial with radial slots and provided with means for setting apart the ends of said fastener means, disposed along the axes of grooves, right up to the cylindrical generatrix of said die and having substantially V-shaped section, each said recess with groove being covered with an individual lid, shaped as an annular segment and rigidly connected to the end face of said die;
   iv) said guiding head having a substantially cylindrical generatrix, a flat or rounded free end, radial slots, evenly arranged in the head body and coming onto its generatrix, as well as outer bulge at the opposite end of said head, the head being mounted with its bulge right up to the individual lids on the end face of said die, radial slots of the guiding head being coaxial with radial slots of the die, and therein said proximal end of pressure rod is movably mounted, and the outer diameter of said cylindrical generatrix of the guiding head is less than the outer diameter of said bulge and said die by a double value of distance assuring the removal from the die a fastener means entirely extended in radial direction;
   v) a means for transmitting axial force from said pressure rod to said fastener means and for converting this axial force into radial forces applied to each of these fastener means, which is necessary for punching via said fastener means the wall of said intravascular device and surrounding wall of a blood vessel so, that the distal ends of the fastener means come in part outside the corresponding blood vessel, to form a rigid connection of said intravascular device to the blood vessel wall.

2. A stapler according to claim 1, wherein said hollow body, substantially cylindrical in shape, has a proximal end and a distal end with the holding handle extending therefrom at a certain angle, up to 90 degrees, and a control lever pivotally mounted on said holding handle.

3. A stapler according to claim 1, wherein the pressure rod disposed inside said hollow body has a longitudinal axis, proximal end, distal end and thrust collar closer to its proximal end, the pressure rod being spring-loaded and operatively connected by its distal end to said control lever, and at its proximal end there is rigidly secured a tip, mounted so as to reciprocate inside said die and said head.

4. A stapler according to claim 1, wherein said die for locating fastener means is shaped as a barrel with a substantially cylindrical generatrix and inner axial cavity, open on the side of the barrel distal end and terminating in a bottom at the proximal end of the barrel, the die having through, evenly arranged radial slots on its bottom, and on the end face of the bottom presented to said guiding head—recesses with grooves for locating fastener means and with means for setting apart the latter, the recesses with grooves have substantially the same depth relatively to said end face of the die bottom, are coaxial with radial slots and each of them is covered with an individual lid, shaped as an annular segment and rigidly connected to the end face of said die.

5. A stapler according to claim 1, wherein said die for locating fastener means is shaped as a barrel with a substantially cylindrical generatrix and inner axial cavity open on the side of said barrel distal end, and terminating in a bottom at the barrel proximal end, the die having through, evenly arranged radial slots on its bottom, and on the end face of the bottom presented to said guiding head—recesses with grooves for locating fastener means, and with means for setting apart the ends of the latter, said recesses with grooves having substantially different depths relative to said end face of the die bottom, being coaxial with radial slots and each of them is covered with an individual lid shaped as an annular segment, the individual lids having an inner surface matching the corresponding recess and being rigidly connected to the end face of said die.

6. A stapler according to claim 5, wherein said recesses with grooves have at least two different depths relative to said end face of the die bottom, the recessed with grooves of different depths being arranged alternately relative to one another.

7. A stapler according to claim 1, wherein said fastener means are substantially U-shaped and disposed radially in said grooves of said stapler die so as to radially extend from said grooves under the action of radial forces, the free ends of said fastener means being disposed on both sides of said means for setting apart the ends of the fastener means, disposed along the axes of grooves, right up to the cylindrical generatrix of said die and substantially V-shaped.

8. A stapler according to claim 7, wherein said means for setting apart the ends of said fastener means are disposed along the axes of grooves, right up to the cylindrical generatrix of said die and are substantially V-shaped, have lateral guiding faces which are substantially curved, concave and diverging from one another in direction from the center of said die to its cylindrical generatrix, which permits to bend outwards the free ends of fastener means when they are extended from the die under the action of said radial forces.

9. A stapler according to claim 7, wherein said means for setting apart the ends of said fastener means are disposed along the axes of grooves, right up to the cylindrical generatrix of said die and have a substantially cylindrical shape, lateral guiding faces, substantially radial, concave and diverging from one another in direction from the center of said die to its cylindrical generatrix which permits to bend outwards the free ends of fastener means when they are extended from the die under the action of said radial forces.

10. A stapler according to claim 1, wherein said guiding head is hollow, and its rounded free end is detachable, capable of being periodically mechanically attached to said head.

11. A stapler according to claim 1, wherein said guiding head is made hollow, with a generatrix shaped as a truncated cone facing by its greater base the rounded free end of this head, and having radial slots evenly arranged in the head body and coming onto its generatrix, as well as an outer bulge at the opposite end of the head, the rounded free end of this head being detachable, capable of being periodically mechanically attached to said head, and the outer diameter of the generatrix of said guiding head is less than the outer diameter of the bulge and the outer diameter of said die by a double value of distance assuring the removal from the die of said fastener means, completely extended in radial direction.

12. A stapler according to claim 1, wherein said guiding head is made hollow, with a curved generatrix, substantially as a paraboloid, widening towards the rounded free end of the head, and has radial slots evenly arranged in the head body and coming onto its generatrix, as well as an outer bulge at the opposite end of the head, the rounded free end of said head being detachable, capable of being periodically mechanically attached to said head, and the outer diameter of the head generatrix close to the bulge is less than the outer diameter of the bulge and outer diameter of said die by a double value of distance assuring the removal from this die said fastener means completely extended in radial direction.

13. A stapler according to claim 1, wherein said means for transmitting axial force from said pressure rod to said fastener means and for converting this axial force into radial forces applied to each of the fastener means is said tip rigidly connected to said pressure rod and provided with pressure ribs, evenly arranged in radial directions about the longitudinal axis of this tip, at its proximal end, to form a single unit, all said pressure ribs having an outer inclined pressure surface and oriented in radial direction so that each rib, in the course of reciprocal movement of the pressure rod, passes in part through the corresponding radial slot of the die and corresponding radial slot of the guiding head for cooperation with the corresponding fastener means.

14. A stapler according to claim 13, wherein each said pressure rib of said tip is shaped substantially as a right triangle with the greater leg oriented along the longitudinal axis of the tip and hypotenuse forming the outer inclined pressure surface, the vertices of all triangular pressure ribs converge to one point at the free end of the tip facing the rounded end of the guiding head.

15. A stapler according to claim 13, wherein each said pressure rib of said tip is shaped substantially as a right-angled trapezium with one side oriented along the longitudinal axis of the tip and second side forming the outer inclined pressure surface, the smaller bases of all trapezoidal pressure ribs converge to the end face at the free end of said tip presented to the rounded end of the guiding head.

16. A stapler according to claims from 14 to 15, wherein said outer inclined pressure surfaces of ribs of said tip are disposed at an angle from 3 to 40 degrees relative to the longitudinal axis of this tip.

17. A stapler according to claim 13, wherein said means for transmitting axial force from said pressure rod to said fastener means and for converting this axial force into radial forces applied to each of these fastener means is the tip rigidly connected to said pressure rod and having pressure ribs evenly arranged in radial directions about the longitudinal axis of this tip, at its proximal end and being integral with one another, as well as additional pushing members shaped as plates, said plates being movably disposed in said radial slots of the die in radial directions about the longitudinal axis of this tip and provided with bearing projections located in said die recesses, the inner ends of these additional pushing members being capable of cooperating with the outer inclined pressure surfaces of ribs of said tip, and the outer ends of these additional pushing members are capable of cooperating with said fastener means disposed in corresponding grooves of said die.

18. A stapler according to one of claims 1, 15 or 17 wherein said die, guiding head, fastener means, disposed in the die grooves, as well as said additional pushing members movably disposed in the radial slots of the die, form, in combination, a single set, removable from the body of said stapler with subsequent replacement by other, similar interchangeable sets.

19. A stapler according to claim 1 additionally provided with an optical system for observing the positioning the stapler working head relative to the surface of a corresponding intravascular device, as well as the location on the surface of fastener means for securing the intravascular device to the wall of a blood vessel, said optical system including at least one optical lens connected via optical fibers to an optical monitor disposed at the surgeon's working place, at least one of said optical fibers intended to light up said spots of locating fastener means for securing the intravascular device to the wall of a blood vessel.

* * * * *